(12) United States Patent
Wright

(10) Patent No.: US 8,428,889 B2
(45) Date of Patent: Apr. 23, 2013

(54) METHODS OF AUTOMATED SPECTRAL PEAK DETECTION AND QUANTIFICATION HAVING LEARNING MODE

(75) Inventor: David A. Wright, Livermore, CA (US)

(73) Assignee: Thermo Finnigan LLC, San Jose, CA (US)

( * ) Notice: Subject to any disclaimer, the term of this patent is extended or adjusted under 35 U.S.C. 154(b) by 315 days.

(21) Appl. No.: 12/900,234

(22) Filed: Oct. 7, 2010

(65) Prior Publication Data

US 2012/0089344 A1 Apr. 12, 2012

(51) Int. Cl.
*G06F 19/00* (2011.01)

(52) U.S. Cl.
USPC .......................................................... 702/32

(58) Field of Classification Search ............ 702/32, 702/85, 179; 703/2, 12
See application file for complete search history.

(56) References Cited

U.S. PATENT DOCUMENTS

| | | | |
|---|---|---|---|
| 4,807,148 | A | 2/1989 | Lacey |
| 5,121,443 | A | 6/1992 | Tomlinson |
| 5,905,192 | A | 5/1999 | Wikfors et al. |
| 6,873,915 | B2 | 3/2005 | Hastings |
| 7,645,984 | B2 | 1/2010 | Gorenstein et al. |
| 7,983,852 | B2 * | 7/2011 | Wright et al. ............ 702/32 |
| 2004/0159783 | A1 | 8/2004 | Gavin et al. |
| 2005/0267689 | A1 | 12/2005 | Tsypin |
| 2010/0100336 | A1 | 4/2010 | Wright et al. |
| 2010/0235105 | A1 | 9/2010 | Volkov et al. |
| 2012/0089342 | A1 * | 4/2012 | Wright ...................... 702/23 |

OTHER PUBLICATIONS

Nelson et al., "Peak Detection and Quantification in NMR Spectra Using the Piqable Algorithm," Bulletin of Magnetic Resonance, p. 290-293, (Jan. 1, 1989).
Highbeam Research, "Applied Biosystems/MDS SCIEX's New Automated Testing Solution Improves Food Contaminant Detection; New Software-Based System Transforms Routine Food Testing Into a More Precise, More Comprehensive and Less Complex Process," Publication: Business Wire, p. 1-5, (May 30, 2006).
Highbeam Research, "Applied Biosystems/MDS SCIEX's Software Development Initiative Targets Drug Discovery With Rapid Analysis of Compounds," Publication: Business Wire, (Feb. 28, 2007).
Highbeam Research, "Applied Biosystems/MDS SCIEX Announces New Proteomics Tools for Biomarker Research," Publication: Business Wire, p. 1-6, (Apr. 23, 2007).
Highbeam Research, "New Forensic Toxicology Application From Applied Biosystems/MDS SCIEX Improves Accuracy of Screening for Drugs of Abuse; New Software Application Supports Greater Confidence in Test Results for Use in Forensic Investigations," Publication: M2 Presswire, p. 1-6, (Oct. 16, 2007).

(Continued)

*Primary Examiner* — Bryan Bui
(74) *Attorney, Agent, or Firm* — Thomas F. Cooney

(57) ABSTRACT

There is provided a method of automatically identifying and characterizing spectral peaks of a spectrum generated by an analytical apparatus comprising the steps of: receiving the spectrum generated by the analytical apparatus; automatically subtracting a baseline from the spectrum so as to generate a baseline-corrected spectrum; automatically detecting and characterizing the spectral peaks in the baseline-corrected spectrum; reporting the detected and characterized spectral peaks to a user; receiving a list of adjustments to be made to the detecting and characterizing step from the user; and adjusting exit values used in the detecting and characterizing step, based on the list of adjustments.

21 Claims, 10 Drawing Sheets

OTHER PUBLICATIONS

Vivo-Truyols et al., "Automatic Program for Peak Detection and Deconvolution of Multi-Overlapped Chromatographic Signals. Part I: Peak Detection," Journal of Chromatograpy, A, Elsevier B.V., 109 (No. 612), p. 133-145, (Jan. 1, 2005).

Vivo-Truyols et al., "Automatic Program for Peak Detection and Deconvolution of Multi-Overlapped Chromatographic Signals. Part II: Peak Model and Deconvolution Algorithms," Journal of Chromatography, A, Elsevier B.V., vol. 109 (No. 612), p. 146-155, (Jan. 1, 2005).

Xue et al., "Automated Peak Tracking for Comprehensive Impurity Profiling in Orthogonal Liquid Chromatographic Separation Using Mass Spectrometric Detection," Journal of Chromatography, A, Elsevier B.V., vol. 105 (No. 02), p. 159-171, (Jan. 1, 2004).

Dixon et al., "An Automated Method for Peak Detection and Matching in Large Gas Chromatography-Mass Spectrometry Data Sets," Journal of Chemometrics (2007), vol. 20 (No. 8-1), p. 325-340, (Jan. 1, 2006).

Lin et al., "Multi-Q: A Fully Automated Tool for Multiplexed Protein Quantitation," Journal of Proteome Research, American Chemical Society, vol. 5 (No. 9), p. 2328-2338, (Jan. 1, 2006).

Hirsch et al., "Quick Analysis of Organophosphurs Pesticides in a Complex Food Matrix," Lebensmittel- & Biotechnologie, Fachverlag (Wien, AU), vol. 18 (No. 4), p. 110-111, (Jan. 1, 2001).

Yu et al., "Identification of In Vitro Metabolites of Indinavir by "Intelligent Automated LC-MS/MS" (INTAMS) Utilizing Triple Quadrupole Tandem Mass Spectrometry," Journal of the American Society for Mass Spectrometry, Elsevier Science Inc., vol. 10 (No. 2), p. 175-183, (Jan. 1, 1999).

Stolt et al.., "Second-Order Peak Detection for Multicomponent High-Resolution LC/MS Data," Analytical Chemistry, American Chemical Society, vol. 78 (4), p. 975-983, (2006).

Keil et al., "Hyphenation of Capillary High-Performance Liquid Chromatography With Matrix-Assisted Laser Desorption/Ionization Time-Of-Flight Mass Spectrometry for Nano-Scale Screening of Single-Bead Combinatorial Libraries," Rapid Commun. Mass Spectrom., vol. 16 (8), p. 814-820, (2002).

Malyarenko et al., "Resampling and Deconvolution of Linear Time-Of-Flight Records for Enhanced Protein Profiling," Rapid Communications in Mass Spectrometry, John Wiley & Sons Ltd., vol. 20 (No. 11), p. 1670-1678, (Jan. 1, 2006).

Veriotti et al., "High-Speed GC and GC/Time-Of-Flight MS of Lemon and Lime Oil Samples," Analytical Chemistry, American Chemical Society, vol. 73 (No. 18), p. 4395-4402, (Jan. 1, 2001).

Rögnvaldsson et al., "Improving Automatic Peptide Mass Fingerprint Protein Identification by Combining Many Peak Sets," Journal of Chromatrography B, Elsevier B.V., vol. 807 (No. 2), p. 209-215, (Jan. 1, 2004).

R. P. Goehner, "Background Subtract Subroutine for Spectral Data," Analytical Chemistry 50 (8), Jul. 1978, p. 1223-1225.

Di Marco et al., "Mathematical Functions for the Representation of Chromatographic Peaks," Journal of Chromatography, vol. 931 (2001), p. 1-30.

Steffen et al., "A New Mathematical Procedure to Evaluate Peaks in Complex Chromatograms," Journal of Chromatography, vol. 1071 (2005), p. 239-246.

Du et al., "Improved Peak Detection in Mass Spectrum by Incorporating Continuous Wavelet Transform-Based Pattern Matching," Bioinformatics, Oxford University Press, vol. 22 (No. 17), p. 2059-2065 (Jul. 4, 2006).

Zhang et al., "Peak Detection With Chemical Noise Removal Using Short-Time FFT for a Kind of MALDI Data ," The First International Symposium on Optimization and Systems Biology (OSB '07), p. 222-231 (Aug. 8, 2007).

\* cited by examiner

METHODS OF AUTOMATED SPECTRAL PEAK DETECTION AND QUANTIFICATION HAVING LEARNING MODE

FIELD OF THE INVENTION

This invention relates to methods of analyzing data obtained from instrumental analysis techniques used in analytical chemistry and, in particular, to methods of automatically identifying peaks in liquid chromatograms, gas chromatograms, mass chromatograms or optical or other spectra without input from or intervention of a user.

BACKGROUND OF THE INVENTION

The various techniques of instrumental analysis used in the broad field of analytical chemistry have been developed and refined primarily over the last century. Many of these techniques involve complex interactions of electromagnetic radiation with samples, possibly containing unknown substances to be identified or characterized. Such techniques include the spectroscopic techniques atomic absorption spectroscopy, atomic emission spectroscopy, UV-visible spectroscopy, infrared spectroscopy, NMR spectroscopy and Raman spectroscopy, among others. Other techniques, such as liquid chromatography (LC), gas chromatography (GC), mass spectrometry (MS) and the hybrid techniques of liquid chromatography-mass spectrometry (LC-MS or HPLC-MS), gas-chromatography-mass spectrometry (GC-MS) and others involve the detection and possibly identification or characterization of various substances derived from mixtures of substances, possibly including unknown analytes, as these substances are separated from one another in a chromatographic column.

One common feature of all the above-listed instrumental techniques is the capability, in use, of generating possibly complex graphs of detected intensity versus some other controlled or measured physical quantity, such as time, frequency, wavelength or mass. Such graphs are generally referred to as "spectra". In this document, the terms "spectroscopy" and "spectrum" are used in a fashion so as to include additional analytical chemical techniques and data that are not strictly concerned with measuring or representing analytical spectra in the electromagnetic realm. Such additional techniques and data include, but are not limited to, mass spectrometry, mass spectra, chromatography and chromatograms (including liquid chromatography, high-performance liquid chromatography and gas chromatography, either with or without coupling to mass spectrograph instrumentation).

Atomic spectroscopic techniques may produce, for each detected element, spectra consisting of multiple lines representing absorption or emission of electromagnetic energy by various electronic transitions of the atomized element. Likewise, molecular spectroscopic techniques may produce spectra of multiple lines or complexly shaped bands representing absorption or emission of electromagnetic energy by various transitions of molecules among or between various excited and/or ground energy states, such energy states possibly being electronic, vibrational or rotational, depending upon the technique employed.

Still further, mass spectrometry techniques may produce complex spectra consisting of several detected peaks, each such peak representing detection of an ion of a particular mass unit. In mass analysis mode, several peaks, of different m/z values (where m represents mass and z represents charge), may be produced as for each ionized species, as a result of both isotopic variation and differing charges. In the various chromatographic techniques, including those techniques (for instance, GC-MS or LC-MS) in which eluting substances are detected by MS as well as those techniques in which detection is by optical spectroscopy, various possibly overlapping peaks of Gaussian or other skewed shapes may be produced as a function of time as the various substances are eluted.

Traditionally, analytical spectroscopy instrumentation has found its greatest use in specialized research or clinical laboratories in which instrument operation and data analysis is performed by personnel who are highly trained and or experienced in the operation and data collection of the particular employed instruments. However, as the use of analytical spectroscopy instrumentation has expanded, in recent years, from specialized research laboratory environments to general industrial, clinical or even public environments for, for instance, high-throughput screening, there has emerged a need to make instrument operation and data collection and interpretation accessible to less highly trained or experienced users. Thus, there is a need for instrument firmware and software to fulfill greater roles in instrument control and data collection, analysis and presentation so as to render overall turnkey high-throughput operation, with minimal user input or intervention.

Historically, in traditional instrumental analysis situations, collected data is analyzed offline with the aid of specialized software. A first step in conventional data analysis procedures is peak picking, so as to identify and quantify spectral peaks. Such chromatographic or spectroscopic peak detection is one of the most important functions performed by any data analysis system. Typically, chromatographic or spectroscopic peak detection software has employed various user-settable parameters, allowing the operator to provide input in the form of initial guesses for peak locations and intensities and subsequently, to "optimize" the results, after execution of some form of fitting routine that employs the operator's guesses as a starting point. Existing methods of peak detection have many adjustable parameters, requiring operator skill and patience in arriving at an acceptable result. Novice or untrained operators will very likely get an incorrect result or no result at all. This typically results in a very time-consuming process, and the "tweaking" by or inexperience of the user often results in data that is not reproducible and suspect. Further, such traditional forms of peak identification are not suitable for high-throughput industrial process monitoring or clinical or other chemical screening operations, in which there may be a requirement to analyze many hundreds or even thousands of samples per day.

Another critical feature in peak detection is integration of the peak area. With regards to many spectra, the area under a resolved peak is proportional to the number of molecules of a particular analyte. Therefore, assessment of the relative abundances of analytes in a sample requires accurate, robust algorithms for peak integration. Prior attempts at providing automated methods (that is, without input of peak parameters by a user or operator) of peak area calculation generally employ algorithms that calculate the area under the graph of the raw spectral data (e.g., by the trapezoidal method of numerical integration) and, as such, may have multiple or inconsistent criteria to determine how far to extend the numerical integration along the flanks of peaks. Also, such prior numerical integration methods handle overlapped peaks poorly, if at all.

Methods termed "parameterless peak detection" are disclosed in a co-pending U.S. patent application Ser. No. 12/255,531, filed Oct. 21, 2008 and published as U.S. Patent Application Publication 2010/0100336, said application assigned to the assignee of the instant invention and incorporated herein by reference in its entirety. The parameterless peak detection methods address previously-identified needs for reproducible methods of automated detection, location and area calculation of peaks that do not require initial parameter input or other intervention by a user or operator. The strength and attraction of parameterless peak detection (PPD) is the automatic nature of the process. With no parameters to adjust, the results are not dependent on the skill of the user and are readily amenable to automated or batch processing. However, in some small percentage of cases, PPD may fail to identify a small peak, or may identify peaks that the user considers to be noise, or may arrive at a peak area that the user considers wrong. In these cases, since there is no way to adjust the PPD process, the user may have to revert to one of the peak detection methods that have adjustable parameters.

SUMMARY

Embodiments in accordance with the present invention provide methods and computer program products for identifying peaks in spectral data that do not require parameter input or intervention by users or instrument operators. Methods in accordance with the present invention do not make a priori assumptions about the particular line shape of the chromatographic or spectroscopic peak(s) and may fit any individual peak to either a Gaussian, exponentially modified Gaussian, Gamma distribution or other form of shape. By not exposing any adjustable parameters to users, methods in accordance with the invention avoid the problems discussed above, and lend themselves to automated analysis. Further, methods in accordance with the invention avoid all the aforementioned problems associated with peak area integration in prior art automated analyses, since the peak area is known from the peak fitting parameters. The present methods may add together multiple Gaussian shapes to yield a final (complex) peak shape or can cleanly separate overlapping peaks that come from different components. Thus, overlapped peaks are easily handled and the integrals computed from the Gaussian (or other) widths and intensities.

To improve the previously described parameterless peak detection techniques, a "learning mode" is provided, wherein the user specifies a peak, or a portion of a peak, (possibly with the cursor of a graphical user interface) and selects from a context menu choices to improve the peak detection for that peak or peak area. If the user specifies a range where no peak is detected, the menu choices provided to the user may be, for instance, "Detect a peak here" and "extend a nearby peak to include this area". If the user specifies a peak, the menu choices may be, for instance, "Don't detect this peak", or "more aggressive peak detection in this area" or "less aggressive peak detection in this area". As in the earlier parameterless peak detection techniques, users generally do not input and are not, in general, exposed to peak modeling parameters.

The learning mode steps allow users to make minor changes in parameterless peak detection in a visual, interactive way. These changes are minor in that they are small changes to the various exit conditions that are already present in the PPD code. Prior to first entry into learning mode, these exit conditions are pre-set based on typical data stream and peak conditions. In order to detect almost all peaks with excellent accuracy, the pre-set exit conditions may permit some small percentage of peaks to be represented with less than optimal parameters. However, the learning mode allows users to fine tune or adapt the procedure to the peculiarities or requirements of any particular experimental data.

In a qualitative setting or environment, the learning mode preference information, as determined from the user's choices, persists while the peak detection software application is open, and can be saved for later use by saving the layout or user preference settings. It may be desirable to save this information automatically when the application is terminated. In a quantitative environment, the learning mode preference information is saved in a quantitation method.

According to first aspect of the invention, there is provided a method of automatically identifying and characterizing spectral peaks of a spectrum generated by an analytical apparatus comprising the steps of:

receiving the spectrum generated by the analytical apparatus;

automatically subtracting a baseline from the spectrum so as to generate a baseline-corrected spectrum;

automatically detecting and characterizing the spectral peaks in the baseline-corrected spectrum;

reporting the detected and characterized spectral peaks to a user;

receiving a list of adjustments to be made to the detecting and characterizing step from the user;

adjusting exit values used in the detecting and characterizing step, based on the list of adjustments; and repeating the automatic detecting and characterizing of the spectral peaks in the baseline-corrected spectrum using the adjusted exit values.

In embodiments, baseline model curve parameters are neither input by nor exposed to the user prior to the reporting step. In embodiments, peak model curve parameters are neither input by nor exposed to the user prior to the reporting step. In some embodiments, the reporting step may include reporting at least one item of information relating to or inferred to relate to at least one operational parameter of the chromatographic instrument. Some embodiments may include the further steps of: automatically estimating a random noise level of the spectrum; and reporting a signal-to-noise (SNR) level relating to the detected peaks to the user. Some embodiments may include automatically determining, for at least one spectral peak, a peak model curve that provides the best fit to said at least one spectral peak from among the group consisting of Gaussian distributions, Gamma distributions and exponentially modified Gaussian distributions.

According to another aspect of the invention, there is a provided a computer readable medium having thereon program instructions for automatically identifying and characterizing spectral peaks of a spectrum generated by an analytical apparatus, the program instructions operable to cause apparatus including a programmable processor to:

receive the spectrum from the analytical apparatus;

automatically subtract a baseline from the spectrum so as to generate a baseline-corrected spectrum;

automatically detect and characterize the spectral peaks in the baseline-corrected spectrum;

report the detected and characterized spectral peak to the user;

receive a list of adjustments to be made to the detecting and characterizing step from the user;

adjust exit values used in the detecting and characterizing step, based on the list of adjustments; and repeat the automatic detecting and characterizing of the spectral peaks in the baseline-corrected spectrum using the adjusted exit values.

The computer readable medium may comprise any external or internal or fixed or portable computer medium and may comprise, for example, a floppy disk, a flash memory device, an optical disk such as a CD or a DVD, a magnetic hard drive, or a memory chip, such device being located either at the same locale as or remote from the programmable processor. If remote from the programmable processor, the programmable processor may read information from computer readable medium over a local or wide area network, over a wireless network, or over the internet.

The steps comprising methods in accordance with the instant invention, as outlined above may be grouped into several basic stages of data processing, each stage possibly comprising several steps. The basic stages referred to above comprise: preprocessing to remove baseline and estimate the noise level; formation of an initial estimate of peak parameters; optional subsequent refinement of these estimates, reporting of results, receiving input from a user in a "learning mode" so as to improve accuracy and precision in subsequent execution of the method and repetition of one or more of the above steps using the same or different data and the user preference information obtained in learning mode. Embodiments in accordance with the invention may include, in the second stage, an algorithm in which the most intense peaks remaining in the observed or processed spectrum are subtracted from the spectrum, one by one, until the residual spectrum contains only noisy fluctuations in the intensities. The detection of peaks in spectra may be performed by a matched filter score that assesses the overlap between a canonical peak shape and a window of intensity samples in the chromatogram. The simplest instance of such a filter score is the value of a single sample intensity. A peak is judged to be present when the filter score exceeds a threshold, defined as a multiple of the estimated noise level. Within certain embodiments, the optional final stage of the algorithm refines the initial parameter estimates for multiple detected chromatographic peaks. Refinement consists of exploring the space of N parameters (the total number of parameters across all peaks, i.e. 4 for each Gamma/EMG and 3 for each Gaussian) to find the set of values that minimizes the sum of squared differences between the observed and model chromatogram.

According to another aspect of the invention, there is a provided a system comprising:

at least one programmable processor unit;

an electronic data storage unit electrically coupled to the programmable processor unit;

user interface hardware electrically coupled to the programmable processor unit;

a spectral peak detection executable module executing on the at least one programmable processor unit and comprising instructions operable to cause the at least one programmable processor unit to read spectral data from the electronic data storage unit and to automatically detect spectral peaks of the spectral data without receiving any parameter input from a user;

a user application executable module executing on the at least one programmable processor unit and in communication with the spectral peak detection executable module and comprising instructions operable to cause the at least one programmable processor and the user interface hardware to present the detected spectral peaks to the user; and a learning mode executable module executing on the at least one programmable processor unit and in communication with the spectral application module and comprising instructions operable to cause the at least one programmable processor to receive a generate a list of adjustments to be made to exit conditions of the peak detection module instructions based on inputs from the user.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The present invention provides methods of automated spectral peak detection and quantification that do not require any user input or intervention during the peak detection process but which do allow for users to interactively teach any particular implementation of the methods how to improve its accuracy and precision in subsequent peak detection processes. The methods described herein can accommodate and model all types of spectral data, where the term "spectral data" is broadly defined as described above, and provide robust automatic detection, integration and reporting of spectral peaks. Any and even all model parameters utilized in these methods may be adaptively determined in a manner that is invisible to the user. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-10, taken in conjunction with the following description.

Figure 1:
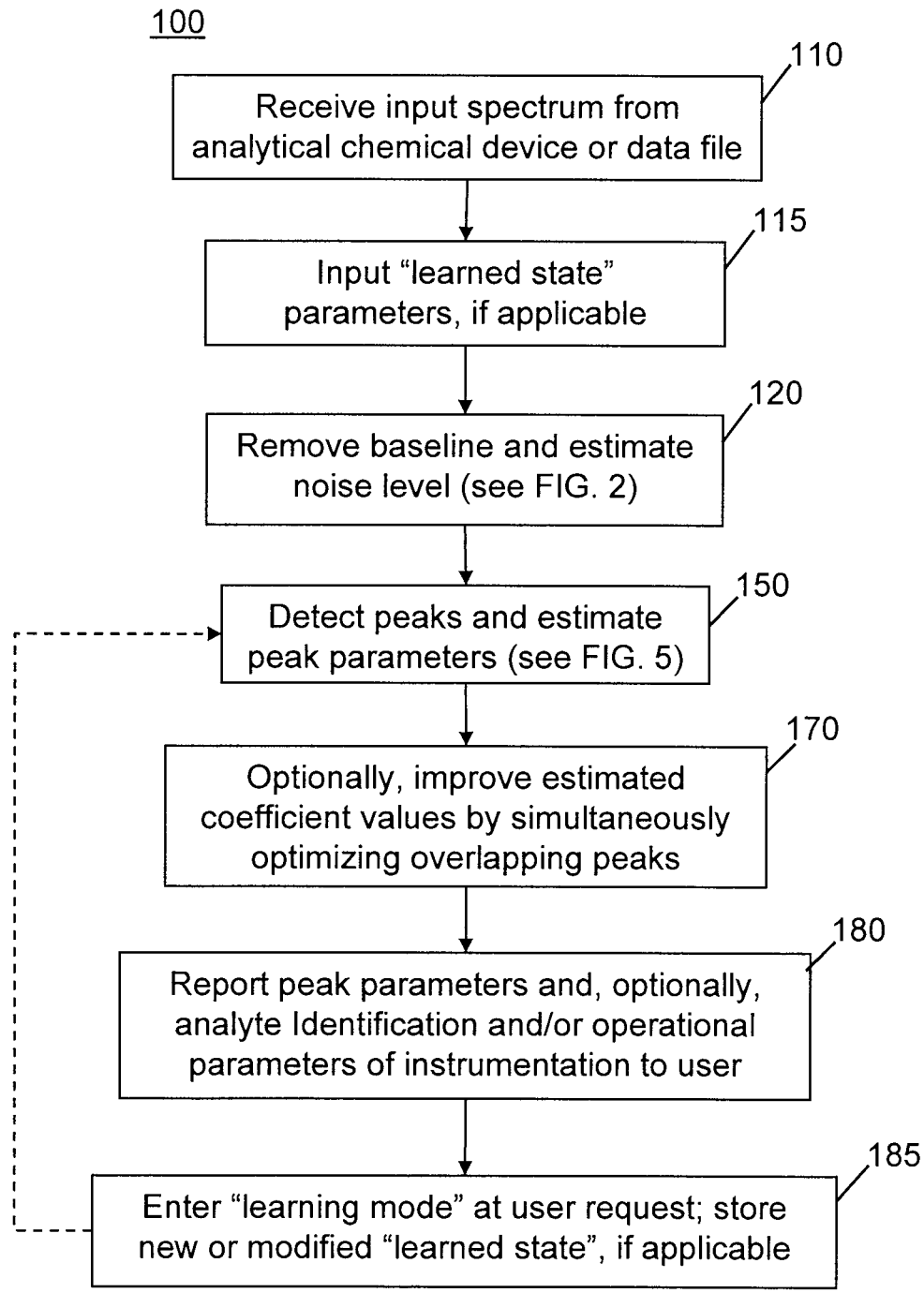
FIG. 1 is a flowchart of a method for automated spectral peak detection and quantification in accordance with an embodiment of the invention.

In embodiments of methods in accordance with the instant invention, the various steps may be grouped into an input step, three basic stages of data processing, each stage possibly comprising several steps, a reporting step, an interactive learning step, and, repetition of one or more of the steps using user preferences determined in the learning step, as outlined in the method 100 as illustrated in FIG. 1. The first step 110 in the method 100 is the reception of an input spectrum directly from an analytical chemical device or, alternatively, from a data file comprising data previously collected from an analytical chemical device. The "spectrum" may, in fact, comprise a chromatogram, such as those produced by liquid or gas chromatography, in which the abscissa represents time (for instance, retention time) and the ordinate represents intensity of detection of analytes or other chemicals by a detector. Alternatively, the spectrum may comprise a mass chromatogram in which a unit of ionic mass is plotted along the abscissa and intensity of detection of ions is plotted along the ordinate. The spectrum may also be any form of recordable spectrum comprising intensity of detected electromagnetic radiation either emitted, scattered or absorbed by a material (or any quantity derivable from such processes) plotted as a function of electromagnetic wavelength or frequency.

Figure 5:
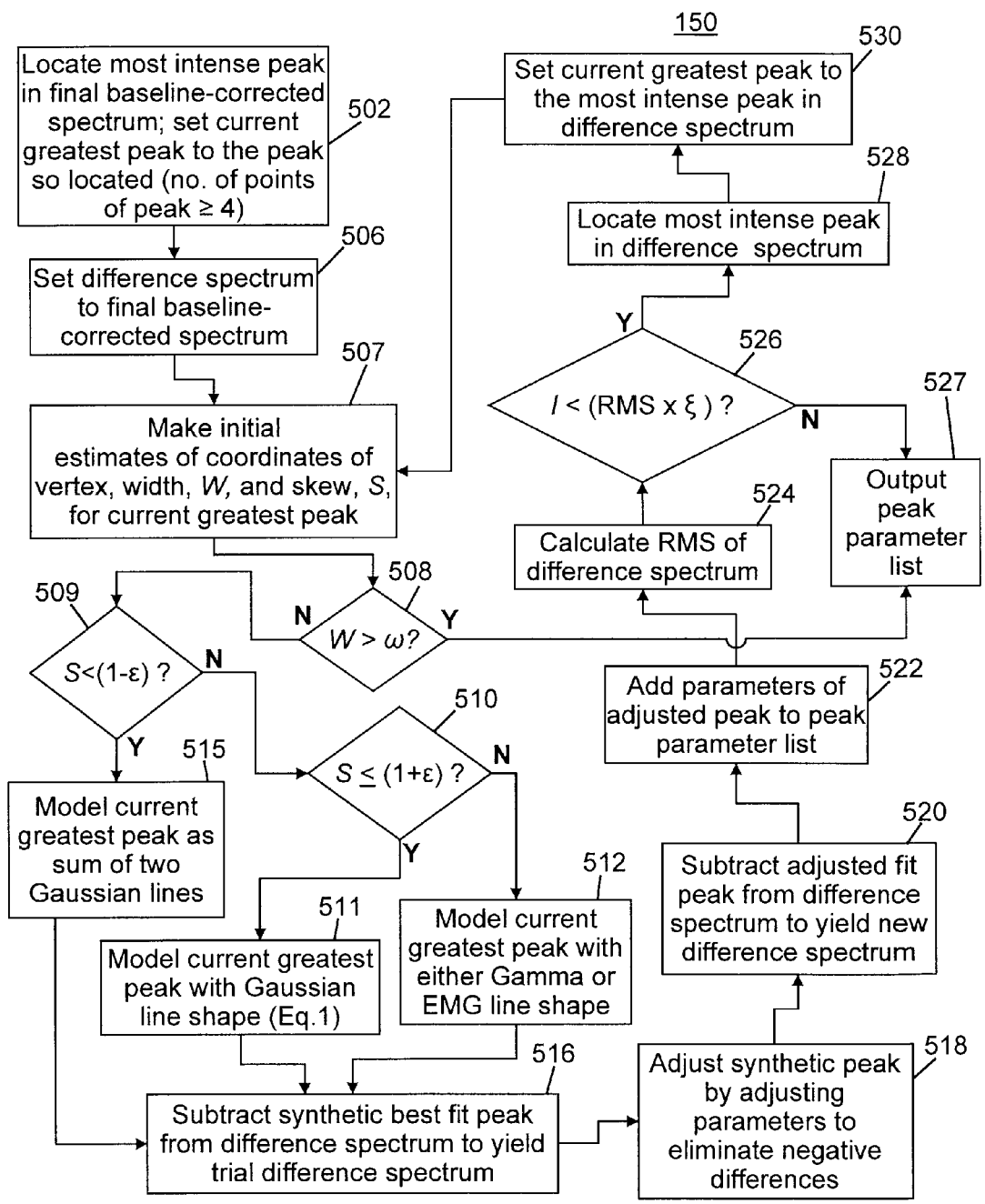
FIG. 5 is a flowchart of a method for automated spectral peak detection and quantification in accordance with an embodiment of the invention.

In the next step, step 115, of the method 100, previously-saved learned-state parameters may be retrieved. The learned-state parameters relate to various exit conditions within the peak detection procedure, as will be described in greater detail in the following discussion. The next step, step 120, is a preprocessing stage in which baseline features may be removed from the received spectrum and in which a level of random "noise" of the spectrum may be estimated, this step being described in greater detail in subsequent FIG. 2. The next step 150, which is described in greater detail in subsequent FIG. 5, is the generation of an initial estimate of the parameters of synthetic peaks, each of which models a positive spectral feature of the baseline corrected spectrum. Such parameters may relate, for instance, to peak center, width, skew and area of modeled peaks, either in preliminary or intermediate form. The subsequent optional step 170 includes refinement of fit parameters of synthetic peaks determined in the preceding step 150 in order to improve the fit of the peaks, taken as a set, to the baseline corrected spectrum. The need for such refinement may depend on the degree of complexity or accuracy employed in the execution of modeling in step 150.

In step 180, the parameters of the final model peaks are reported to a user. The reporting may be performed in numerous alternative ways—for instance via a visual display terminal, a paper printout, or, indirectly, by outputting the parameter information to a database on a storage medium for later retrieval by a user or by a combination of these reporting methods. The reporting step may include reporting either textual or graphical information, or both. This reporting step 180 may include the additional actions of comparing peak parameters (for instance, peak position) to a database and reporting, to a user, the identities of analytes that correspond to one or more peaks. Some methods of the invention may further include, in step 180, the action of extracting, from the model spectral parameters, information related to or inferred to be related to the physical functioning or operational state or an operational parameter of an analytical instrument that provided the spectral data and reporting such instrument-related information to a user.

Upon review of the reported information, a user may elect to enter learning mode, step 185. The learning mode module manages the collection of adjustments that will be applied to the PPD process (called a "learned state"), and has means to allow the user to create, modify, delete, and set as a default any learned state (step 185). Execution may then branch back to step 150 so as to re-detect peaks, of the same spectrum, using a learned state recently stored, created, modified or set as a default in the step 185.

The term "model" and its derivatives, as used herein, may refer to either statistically finding a best fit synthetic peak or, alternatively, to calculating a synthetic peak that exactly passes through a limited number of given points. The term "fit" and its derivatives refer to statistical fitting so as to find a best-fit (possibly within certain restrictions) synthetic peak such as is commonly done by least squares analysis. Note that the method of least squares (minimizing the chi-squared metric) is the maximum likelihood solution for additive white Gaussian noise. In other situations (e.g., photon-counting), it might be appropriate to minimize a different error metric, as directed by the maximum likelihood criterion. More detailed discussion of individual method steps and alternative methods is provided in the following discussion and associated figures.

Baseline Detection

A feature of a first, pre-processing stage of the new methods of peak detection takes note of the concept that (disregarding, for the moment, any chemical or electronic noise) a spectroscopic signal (such as, for instance, a chromatogram which is a signal obtained versus time) consists of signal plus baseline. If one can subtract the baseline correctly, everything that remains must be signal, and should be fitted to some sort of data peak.

Figure 2:
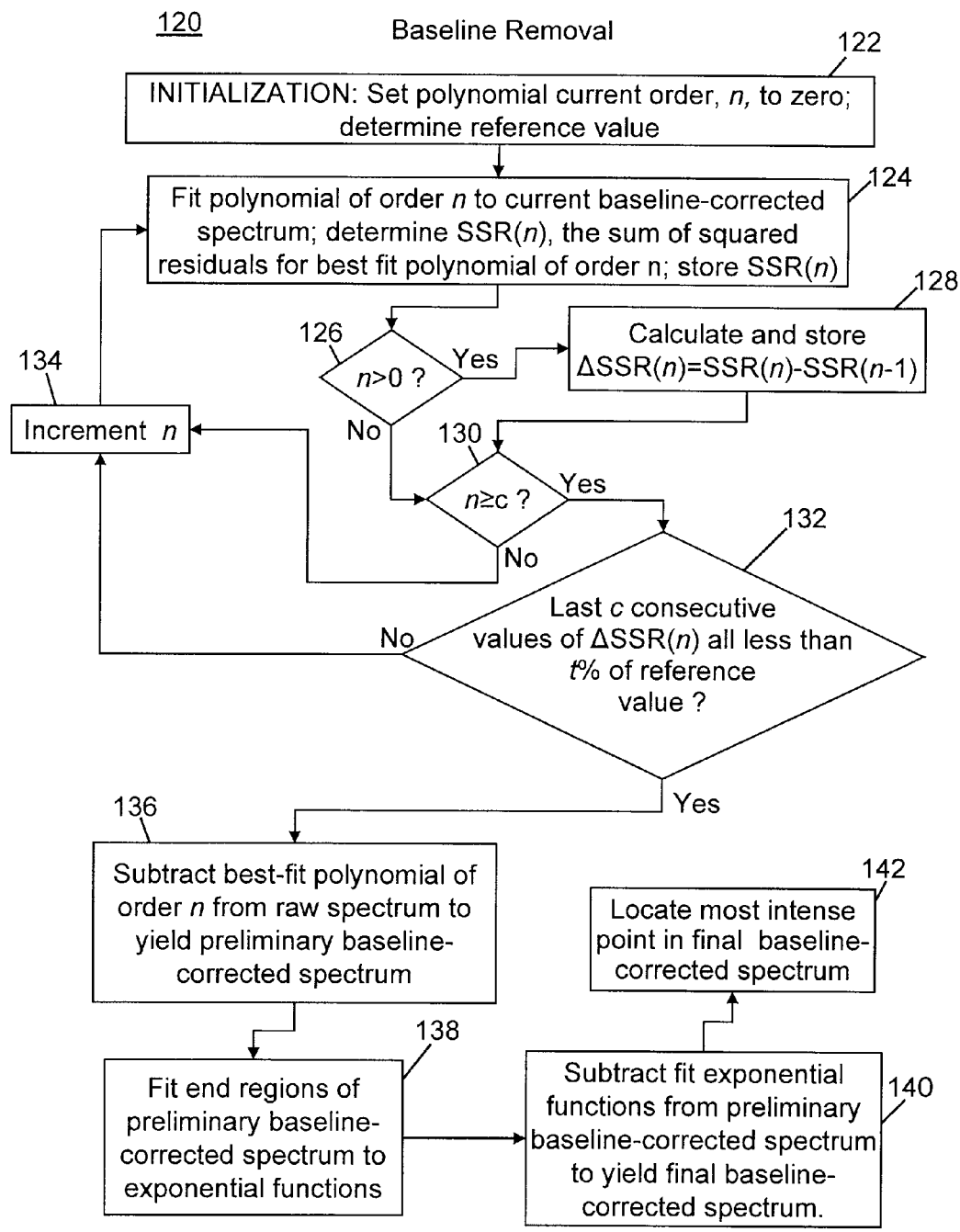
FIG. 2 is a flowchart of a method for automatically removing baseline features and estimating background noise from spectral data in accordance with an embodiment of the invention.

Therefore, embodiments in accordance with the present invention may start by determining the correct baseline. Steps in the methods may apply a polynomial curve as the baseline curve, and measure the residual (the difference between the chromatographic data and the computed baseline) as a function of polynomial order. For instance, FIG. 2 illustrates a flowchart of a method 120 for automatically removing baseline features from spectral data in accordance with some embodiments of the invention. The method 120 illustrated in FIG. 2 repeatedly fits a polynomial function to the baseline, subtracts the best fit polynomial function from the spectrum so as to provide a current baseline-corrected spectrum, evaluates the quality of the fit, as measured by a sum of squared residuals (SSR), and proceeds until SSR changes, from iteration to iteration, by less than some pre-defined percentage of its original value for a pre-defined number of iterations.

Figure 3:
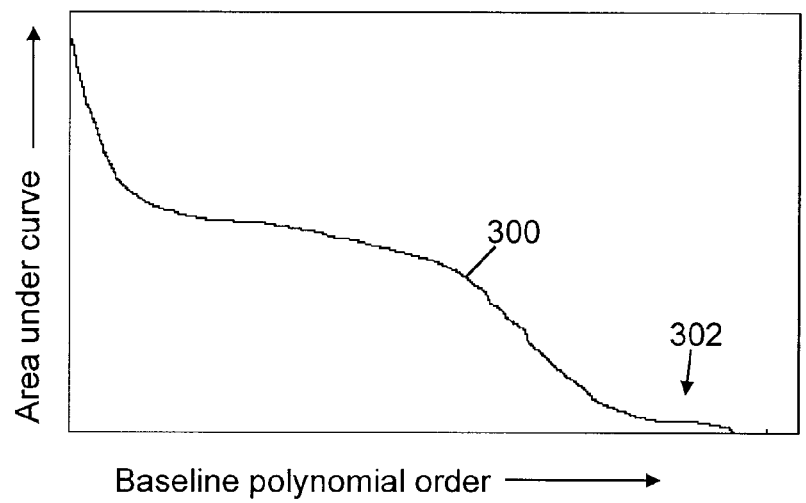
FIG. 3 is a graph of an example of the variation of the calculated area underneath a baseline-corrected spectral curve as a function of the order of polynomial used in fitting the baseline to a polynomial function.

FIG. 3 is an exemplary graph 300 of the variation of the calculated area underneath a baseline-corrected spectral curve as a function of increasing order of the polynomial used in fitting the baseline. FIG. 3 shows that the area initially decreases rapidly as the order of the best fit polynomial increases. This function will go from some positive value at order zero, to a value of zero at some high polynomial order. However, as may be observed from FIG. 3, after most of the baseline curvature has been fit, the area function attains a plateau region 302 for which the change in the function between polynomial orders is some relatively small amount (for instance 5% of its initial value). At this point, the polynomial-fitting portion of the baseline determination routine may be terminated.

To locate the plateau region 302 as indicated in FIG. 3, methods according to the present invention may repeatedly compute the sum of squared residuals (SSR) for sequential values of polynomial order, each time computing the difference of the SSR (ΔSSR) determined between consecutive polynomial orders. This process is continued until a region is found in which the change (ΔSSR) is less than the pre-defined percentage (for instance, 5%) of a certain reference value determined from the spectrum for a certain number c (for instance, four) of sequential iterations. The reference value may comprise, for instance, the maximum intensity of the original raw spectrum. Alternatively, the reference value may comprise the sum of squared values ($SSV_0$) of the original raw spectrum or some other quantity calculated from the spectral values.

Once it is found that ΔSSR less than the pre-defined percentage of the reference value for c iterations, then one of the most recent polynomial orders (for instance, the lowest order of the previous four) is chosen as the correct polynomial order. The subtraction of the polynomial with the chosen order yields a preliminary baseline corrected spectrum, which may perhaps be subsequently finalized by subtracting exponential functions that are fit to the end regions.

Returning, now, to the discussion of method 120 shown in FIG. 2, it is noted that the first step 122 comprises loop initialization step of setting the order, n, of the baseline fitting polynomial to an initial value of zero and determining a reference value to be used, in a later step 132, for determining when the fitting polynomial provides an adequate fit to the baseline. The reference value may simply be the maximum intensity of the raw spectrum. Alternatively, the reference value may be some other measure determined from the spectrum, such as the sum of the squared values (SSV) of the spectrum.

From step 122, the method 120 proceeds to a step 124, which is the first step in a loop. The step 124 comprises fitting a polynomial of the current order (that is, determining the best fit polynomial of the current order) to the raw spectrum by the well-known technique of minimization of a sum of squared residuals (SSR). The SSR as a function of n, SSR(n) is stored at each iteration for comparison with the results of other iterations.

From step 124, the method 120 proceeds to a decision step 126 in which, if the current polynomial order n is greater than zero, then execution of the method is directed to step 128 in order to calculate and store the difference of SSR, ΔSSR(n), relative to its value in the iteration just prior. In other words, ΔSSR(n)=SSR(n)−SSR(n−1). The value of ΔSSR(n) may be taken a measure of the improvement in baseline fit as the order of the baseline fitting polynomial is incremented to n.

The iterative loop defined by all steps from step 124 through step 132, inclusive, proceeds until SSR changes, from iteration to iteration, by less than some pre-defined percentage, t %, of the reference value for a pre-defined integer number, c, of consecutive iterations. Thus, the number of completed iterations, integer n, is compared to c in step 130. If n≧c, then the method branches to step 132, in which the last c values of ΔSSR(n) are compared to the reference value. However, in the alternative situation (n<c), there are necessarily fewer than c recorded values of ΔSSR(n), and step 132 is bypassed, with execution being directed to step 134, in which the integer n is incremented by one.

The sequence of steps from step 124 up to step 132 (going through step 128, as appropriate) is repeated until it is determined, in step 132, that the there have been c consecutive iterations in which the SSR value has changed by less than t % of the reference value. At this point, the polynomial portion of baseline correction is completed and the method branches to step 136, in which the final polynomial order is set and a polynomial of such order is subtracted from the raw spectrum to yield a preliminary baseline-corrected spectrum.

Figure 4:
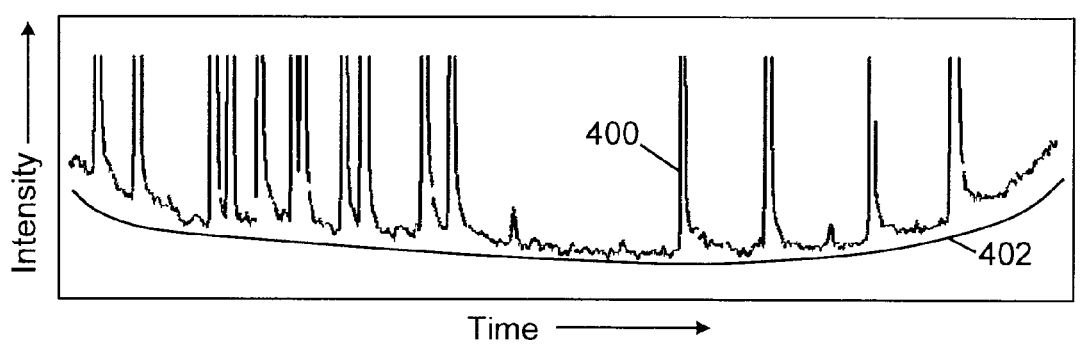
FIG. 4 is an example of a preliminary baseline corrected spectral curve prior to fitting the end regions to exponential functions and an example of the baseline comprising exponential fit functions.

The polynomial baseline correction is referred to as "preliminary" since, as the inventors have observed, edge effects may cause the polynomial baseline fit to be inadequate at the ends of the data, even though the central region of the data may be well fit. FIG. 4 shows an example of such a preliminary baseline corrected spectrum 400. The residual baseline curvature within the end regions (for instance, the leftmost and rightmost 20% of the spectrum) of the spectrum 400 are well fit by a sum of exponential functions (one for each end region), the sum of which is shown in FIG. 4 as curve 402. Either a normal or an inverted (negated) exponential function may be employed, depending on whether the data deviates from zero in the positive or negative direction. This correction may be attempted at one or both ends of the spectrum. Thus, the method 120 proceeds to step 138 which comprises least squares fitting of the end region baselines to exponential functions, and then to step 140 which comprises subtraction of these functions from the preliminary baseline-corrected spectrum to yield the final baseline corrected spectrum. These steps yield a final baseline-corrected spectrum. In step 142, the most intense point in the final baseline spectrum is located.

Peak Detection

At this point, after the application of the steps outlined above, the baseline is fully removed from the data and the features that remain within the spectrum above the noise level may be assumed to be analyte signals. The methods described in FIG. 5 locate the most intense region of the data, fit it to one of several peak shapes, remove that theoretical peak shape from the experimental data, and then continue to repeat this process until there are no remaining data peaks with a signal-to-noise ratio (SNR) greater than some pre-determined value, s, greater than or equal to unity. The steps of this process are illustrated in detail in FIG. 5 and also shown in FIG. 1. The pre-defined value, s, may be chosen so as to limit the number of false positive peaks. For instance, if the RMS level of Rayleigh-distributed noise is sigma, then a peak detection threshold, s, of 3 sigma leads to a false detection rate of about 1%.

The method 150, as shown in FIG. 5 is an iterative process comprising initialization steps 502 and 506, loop steps 507-530 (including loop exit decision step 526) and final reporting step 527. A new respective peak is located and modeled during each iteration of the loop defined by the sequence of steps 507-530.

The first step 502 of method 150 comprises locating the most intense peak in the final baseline-corrected spectrum and setting a program variable, current greatest peak, to the peak so located. In this discussion, the terms "peak" or "spectrum" are used to refer to curves (that is, either an array of x,y Cartesian coordinate pairs or, in reference to a synthetic peak, possibly a function y=f(x)) that may be considered as sub-spectra (and which may be an entire spectrum) and which may be defined on a certain subset (which may be the full set) of the available range of x-axis data. The variable x may represent time, wavelength, etc. and y generally, but not necessarily, represents intensity. Accordingly, it is to be kept in mind that, as used in this discussion, the acts of locating a peak or spectrum, setting or defining a peak or spectrum, performing algebraic operations on a peak or spectrum, etc. implicitly involve either point-wise operations on sets of points or involve operations on functional representations of sets of points. Thus, for instance, the operation of locating the most intense peak in step 502 involves locating all points in the vicinity of the most intense point that are above a presumed noise level, under the proviso that the total number of points defining a peak must be greater than or equal to four. Also, the operation of "setting" a program variable, current greatest peak, comprises storing the data of the most intense peak as an array of data points.

From step 502, the method 150 proceeds to second initialization step 506 in which another program variable, "difference spectrum" is set to be equal to the final baseline-corrected spectrum (see step 140 of method 120, FIG. 2). The difference spectrum is a program variable that is updated during each iteration of the loop steps in method 150 so as to keep track of the spectrum resulting from subtraction of all prior-fitted peaks from the final baseline-corrected spectrum. As discussed later in this document, the difference spectrum is used to determine when the loop is exited under the assumption that, once all peaks have been located and modeled, the difference spectrum will consist only of "noise".

Figure 6:
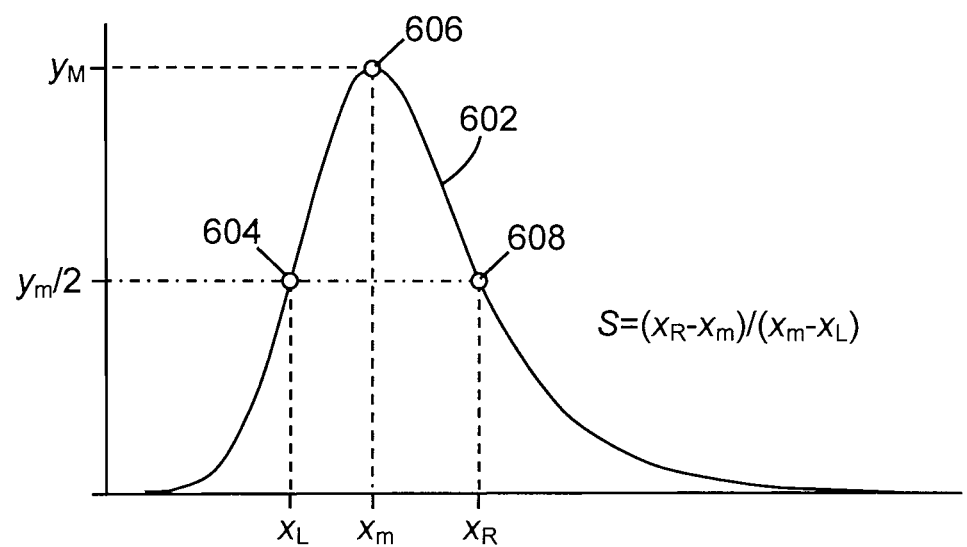
FIG. 6 a graph of a hypothetical skewed spectral peak depicting a method in accordance with the invention for obtaining three points on the spectral peak to be used in an initial estimate of skew and for preliminary peak fitting.

Subsequently, the method 150 enters a loop at step 507, in which initial estimates are made of the coordinates of the peak maximum point and of the left and right half-height points for the current greatest peak and in which peak skew, S is calculated. The method of estimating these co-ordinates is schematically illustrated in FIG. 6 and is discussed in greater detail later with respect to FIGS. 8A-8B. Letting curve 602 of FIG. 6 represent the current greatest peak, then the co-ordinates of the peak maximum point 606, left half-height point 606 and right half-height point 608 are, respectively, $(x_m, y_m)$, $(x_L, y_m/2)$ and $(x_R, y_m/2)$. The peak skew, S, is then defined as: $S=(x_R-x_m)/(x_m-x_L)$.

In step 508, the estimated peak width, W, is compared to a maximum allowable width, $\omega$, which may, for example, be determined according to a maximum proportion of the entire spectrum width. If the width, W, of the alleged peak is too large, then the peak is, most likely, not an actual spectral peak but an indication of residual baseline curvature and the method branches to the termination step 527. Otherwise, the method proceeds to steps 509 and 510.

In steps 509 and 510, the peak skew, S, may be used to determine a particular form (or shape) of synthetic curve (in particular, a distribution function) that will be subsequently used to model the current greatest peak. Thus, in step 509, if $S<(1-\epsilon)$, where $\epsilon$ is some pre-defined positive number, such as, for instance, $\epsilon=0.05$, then the method 150 branches to step 515 in which the current greatest peak is modeled as a sum of two Gaussian distribution functions (in other words, two Gaussian lines). Otherwise, in step 510, if $S\leq(1+\epsilon)$, then the method 150 branches to step 511 in which a (single) Gaussian distribution function is used as the model peak form with regard to the current greatest peak. Otherwise, the method 150 branches to step 512, in which either a gamma distribution function or an exponentially modified Gaussian (EMG) or some other form of distribution function is used as the model peak form. A non-linear optimization method such as the Marquardt-Levenberg Algorithm (MLA) or, alternatively, the Newton-Raphson algorithm may be used to determine the best fit using any particular line shape. After either step 511, step 512 or step 515, the synthetic peak resulting from the modeling of the current greatest peak is removed from the spectral data (that is, subtracted from the current version of the "difference spectrum") so as to yield a "trial difference spectrum" in step 516. Additional details of the gamma and EMG distribution functions and a method of choosing between them are discussed in greater detail, partially with reference to FIG. 8, later in this document.

Occasionally, the synthetic curve representing the statistical overall best-fit to a given spectral peak will lie above the actual peak data within certain regions of the peak. Subtraction of the synthetic best fit curve from the data will then necessarily introduce a "negative" peak artifact into the difference spectrum at those regions. Such artifacts result purely from the statistical nature of the fitting process and, once introduced into the difference spectrum, can never be subtracted by removing further positive peaks. However, physical constraints generally require that all peaks should be positive features. Therefore, an optional adjustment step is provided as step 518 in which the synthetic peak parameters are adjusted so as to minimize or eliminate such artifacts.

In step 518 (FIG. 5), the solution space may be explored for other fitted peaks that have comparable squared differences but result in residual positive data. A solution of this type is selected over a solution that gives negative residual data. Specifically, the solution space may be incrementally walked so as to systematically adjust and constrain the width of the synthetic peak at each of a set of values between 50% and 150% of the width determined in the original unconstrained least squares fit. After each such incremental change in width, the width is constrained at the new value and a new least squared fit is executed under the width constraint. The positive residual (the average difference between the current difference spectrum and the synthetic peak function) and chi-squared are calculated and temporarily stored during or after each such constrained fit. As long as chi-squared doesn't grow beyond a certain multiple of its initial value, for instance 3-times its initial value, the search continues until the positive residual decreases to below a certain limit, or until the limit of peak width variation is reached. This procedure results in an adjusted synthetic fit peak which, in step 520, is subtracted from the prior version of the difference spectrum so as to yield a new version of the difference spectrum (essentially, with the peak removed). In step 522, information about the most recently adjusted synthetic peak, such as parameters related to peak form, center, width, shape, skew, height and/or area are stored.

In step 524, the root-of-the-mean squared values (root-mean-square or RMS) of the difference spectrum is calculated. The ratio of this RMS value to the intensity of the most recently synthesized peak may be taken as a measure of the signal-to-noise (SNR) ratio of any possibly remaining peaks. As peaks continue to be removed (that is, as synthetic fit peaks are subtracted in each iteration of the loop), the RMS value of the difference spectrum approaches the RMS value of the noise. As each tentative peak is found, its maximum intensity, I, is compared to the current RMS value, and if $I<(RMS\times\xi)$ where $\xi$ is a certain pre-defined noise threshold value, greater than or equal to unity, then further peak detection is terminated. Thus, the loop termination decision step 526 utilizes such a comparison to determine if any peaks of significant intensity remain distinguishable above the system noise. If there are no remaining significant peaks present in the difference spectrum, then the method 150 branches to the final reporting step 527. However, if data peaks are still present in the residual spectrum, the calculated RMS value will be larger than is appropriate for random noise and at least one more peak must be fitted and removed from the residual spectrum. In this situation, the method 150 branches to step 528 in which the most intense peak in the current difference spectrum is located and then to step 530 in which the program variable, current greatest peak, is set to the most intense peak located in step 528. The method then loops back to step 507, as indicated in FIG. 5.

Now that the overall set of steps in the method 150 have been described, the process that is used to model individual spectral features is now discussed in greater detail. Traditional spectral peak fitting routines generally model spectral features using either a Gaussian or Lorentzian forms (commonly referred to as peak shapes or line shapes) and tend to either use one preferred line shape throughout the fitting procedure or to query a user as to which line shape to use. Although any arbitrary peak shape can be modeled with a sum of Gaussians (perhaps requiring some Gaussians with negative intensities), the inventors have observed that commonly occurring natural peak shapes (especially in chromatographic spectral data) include Gaussians or even Gamma-distribution-like functions with tailing or leading edges. Therefore, methods in accordance with the present invention may employ a library of peak shapes containing at least four curves (and possibly others) to model observed peaks: a Gaussian for peaks that are nearly symmetric; a sum of two Gaussians for peaks that have a leading edge (negative skewness); a and either an exponentially modified Gaussian or a Gamma distribution function for peaks that have a tailing edge (positive skewness).

The modeling of spectral peaks with Gaussian line shapes is well known and will not be described in great detail here. Methods in accordance with the invention may use a Gaussian functional form that utilizes exactly three parameters for its complete description, these parameters usually being taken as area A, mean $\mu$ and variance $\sigma^2$ in the defining equation:

$$I(x; A, \mu, \sigma^2) = \frac{A}{\sigma\sqrt{2\pi}} \exp\left(-\frac{(x-\mu)^2}{2\sigma^2}\right). \quad \text{Eq. 1}$$

in which x is the variable of spectral dispersion (generally the independent variable or abscissa of an experiment or spectral plot) such as wavelength, frequency, or time and I is the spectral ordinate or measured or dependent variable, possibly dimensionless, such as intensity, counts, absorbance, detector current, voltage, etc. Note that a normalized Gaussian distribution (having a cumulative area of unity and only two parameters—mean and variance) would model, for instance, the probability density of the elution time of a single molecule. In the three-parameter model given in Eq. 1, the scale factor A may be taken as the number of analyte molecules contributing to a peak multiplied by a response factor.

As is known, the functional form of Eq. 1 produces a symmetric line shape (skew, S, equal to unity) and, thus, step 511 in the method 150 (FIG. 5) utilizes a Gaussian line shape when the estimated peak skew is in the vicinity of unity, that is when $(1-\epsilon) \leq S \leq (1+\epsilon)$ for some positive quantity $\epsilon$. In the illustration shown in FIG. 5, the quantity $\epsilon$ is taken as 0.05, but it could be any other pre-defined positive quantity. A statistical fit may performed within a range of data points established by a pre-defined criterion. For instance, the number of data points to be used in the fit may be calculated by starting with a pre-set number of points, such as 12 points and then adjusting, either increasing or decreasing, the total number of data points based on an initial estimated peak width. Preferably, downward adjustment of the number of points to be used in the fit does not proceed to less than a certain minimum number of points, such as, for instance, five points.

Alternatively, the fit may be mathematically anchored to the three points shown in FIG. 6. Alternatively, the range of the fit may be defined as all points of the peak occurring above the noise threshold. Still further alternatively, the range may be defined via some criterion based on the intensities of the points or their intensities relative to the maximum point 606, or even on criterion based wholly or in part on calculation time. Such choices will depend on the particular implementation of the method, the relative requirements for calculation speed versus accuracy, etc.

Figure 7A:
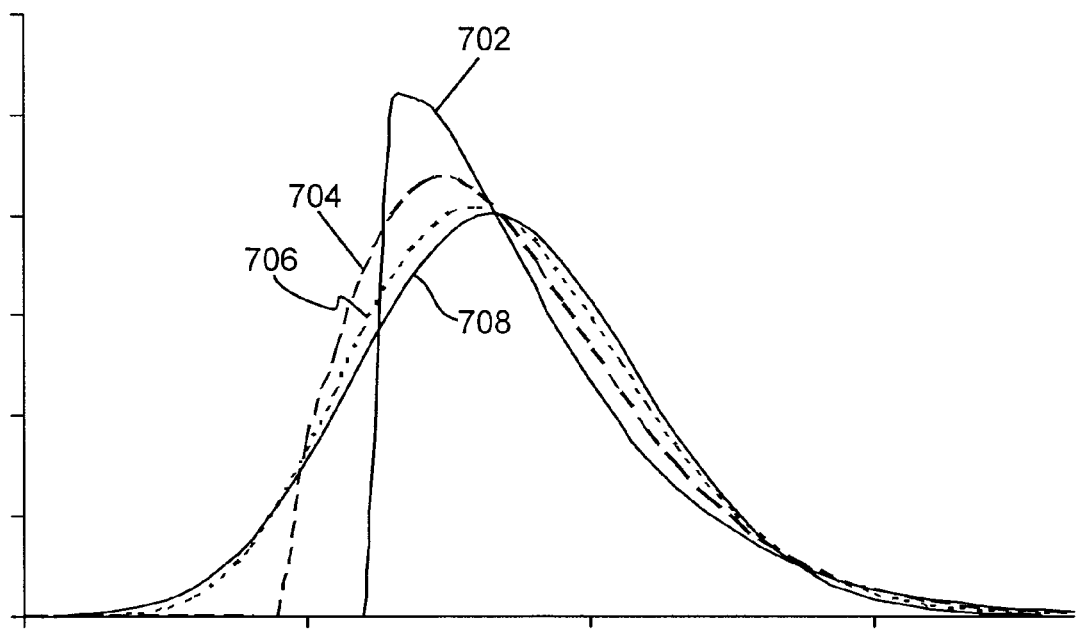
FIG. 7A a graph of a set of gamma distribution functions having different values of shape parameter M, illustrating a fashion by such functions may be used to synthetically fit skewed spectral peaks.

If $S>(1+\epsilon)$, then the data peak is skewed so as to have an elongated tail on the right-hand side. This type of peak may be well modeled using either a line shape based on either the Gamma distribution function or on an exponentially modified Gaussian (EMG) distribution function. Examples of peaks that are skewed in this fashion (all of which are synthetically derived Gamma distributions) are shown in FIG. 7A. If the peaks in FIG. 7A are taken to be chromatograms, then the abscissa in each case is in the units of time, increasing towards the right. The inventors have observed that peaks with this form of skew ($S>(1+\epsilon)$ with $\epsilon>0$, termed "peak tailing") are common in chromatographic data.

The general form of the Gamma distribution function, as used herein, is given by:

$$I(x; A, x_0, M, r) = A \frac{r^M (x-x_0)^{M-1} e^{-r(x-x_0)}}{\Gamma(M)} \quad x \geq x_0 \qquad \text{Eq. 2}$$

in which the dependent and independent variables are x and I, respectively, as previously defined, $\Gamma(M)$ is the Gamma function, defined by $$\Gamma(M) = \int_0^\infty u^{M-1} e^{-u} du$$

and are A, $x_0$, M and r are parameters, the values of which are calculated by methods of the invention. Note that references often provide this in a "normalized" form (i.e., a probability density function), in which the total area under the curve is unity and which has only three parameters. However, as noted previously herein, the peak area parameter A may be taken as corresponding to the number of analyte molecules contributing to the peak multiplied by a response factor.

The inventors consider that a chromatographic peak of a single analyte exhibiting peak tailing may be modeled by a four-parameter Gamma distribution function, wherein the parameters may be inferred to have relevance with regard to physical interaction between the analyte and the chromatographic column. In this case, the Gamma function may be written as:

$$I(t; A, t_0, M, r) = A \frac{r^M (t-t_0)^{M-1} e^{-r(t-t_0)}}{\Gamma(M)} \quad t \geq t_0 \qquad \text{Eq. 2a}$$

in which t is retention time (the independent variable), A is peak area, $t_0$ is lag time and M is the mixing number. Note that if M is a positive integer then $\Gamma(M)=(M-1)!$ and the distribution function given above reduces to the Erlang distribution. The adjustable parameters in the above are A, $t_0$, M and r. FIG. 7A illustrates four different Gamma distribution functions for which the only difference is a change in the value of the mixing parameter, M. For curves 702, 704, 706 and 708, the parameter M is given by M=2, M=5, M=20 and M=100, respectively. In the limit of high M, the Gamma function approaches the form of a Gaussian function.

Figure 7B:
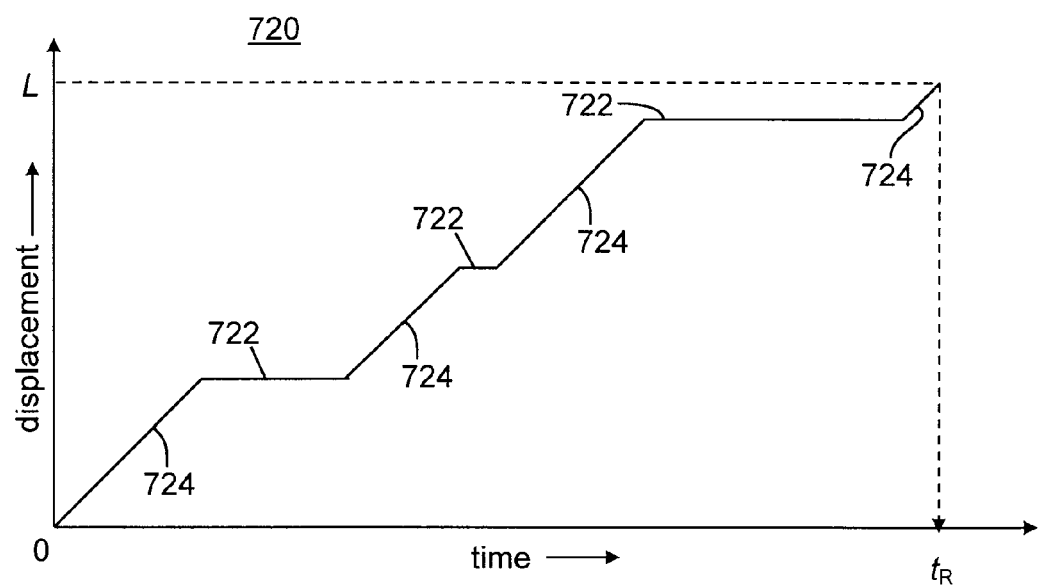
FIG. 7B is a schematic illustration of a theoretical model of movement of a molecule in a chromatographic column during mass chromatography showing alternations between mobile and stationary phases wherein random desorption from the stationary phase is governed by a homogeneous rate constant.

FIG. 7B is a schematic illustration of a theoretical model of movement of a molecule in a chromatographic column during mass chromatography. The abscissa of FIG. 7B shows elution time running from zero up to the retention time $t_R$ and the ordinate represents displacement distance of an analyte through the column, starting from the column inlet up to the full length, L, of the column. In the inventors' model, molecules of the analyte alternate between mobile and stationary phases a finite number, M, (see Eq. 2) of times within the column. It is further assumed that all molecules of the same analyte have nearly the same M and that the value of M for each analyte may be inferred from its peak shape in the chromatogram. At those times when an analyte molecule is in the mobile phase, it is assumed to travel at a constant velocity v through the column and the displacement within the column is represented by slanting line segments 724 of constant and non-zero slope. The total time μ that the molecule resides in the mobile phase is the simple expression given as μ=L/v which represents a delay that shifts all peaks to the right by the same amount. This delay, along with other factors, such as dead volume, is encapsulated in the parameter $t_0$ (see Eq. 2). In the inventors' model, it is assumed that mobile phase velocity v is constant for a given analyte and, thus, the occurrence of "multiple paths" and longitudinal diffusion is negligible.

Continuing with the discussion of FIG. 7B, it is assumed that during those times when an analyte molecule resides in the stationary phase, it does not move at all. These times are represented by the horizontal line segments 722. In the inventors' model, it is further assumed that the desorption of an analyte molecule from the stationary phase is a Poisson process and that the probability of desorption is homogeneous in time. Therefore the duration of analyte adsorption (that is, the length of the horizontal line segments 722 in FIG. 7B) is a random variable λ given by an exponential probability density distribution function having parameter r (see Eq. 2).

With the assumptions given above, the total retention time $t_R$ of an analyte is a random variable given by the expression $t_R = L/v + \Sigma_{m=1}^{M} \lambda_m$ in which the summation is taken over a total of M independent exponentially distributed random variables. If M is an integer, then the summation shown in the above equation yields an Erlang-distributed random variable. In fact, the value of M would be Poisson distributed in a population of molecules, so the retention time would be modeled by the superposition of multiple Erlang random variables. A simple closed-form approximation can be constructed by replacing the distribution of values of M with a constant value that may be loosely interpreted as the mean value of M. The generalization of the Erlang distribution to real-valued M is the Gamma distribution (Eq. 2).

The Gamma distribution model as derived above does not specifically account for chemical diffusion. The presence of diffusion is accommodated by values of M which are, in fact, larger than the average number of desorption events. A different model, the exponentially modified Gaussian (EMG) distribution function, may be used to model the retention time as the outcome of one desorption event and the time required for an analyte molecule to diffuse to the end of the column.

The general, four-parameter form of the exponentially modified Gaussian (EMG) distribution, as used in methods according to the present invention, is given by a function of the form:

$$I(x; A, x_0, \sigma^2, \tau) = A \int_{-\infty}^{x} \frac{1}{\sigma\sqrt{2\pi}} e^{-(u-x_0)^2/2\sigma^2} \frac{1}{\tau} e^{-(x-u)/\tau} du \ (x \geq 0; \tau > 0). \quad \text{Eq. 3}$$

Thus, the EMG distribution used herein is defined as the convolution of an exponential distribution with a Gaussian distribution. In the above Eq. 3, the independent and dependent variables are x and I, as previously defined and the parameters are A, $t_0$, $\sigma^2$, and τ. The parameter A is the area under the curve and is proportional to analyte concentration and the parameters $t_0$ and $\sigma^2$ are the centroid and variance of the Gaussian function that modifies an exponential decay function.

The inventors consider that an exponentially-modified Gaussian distribution function of the form of Eq. 3 may be used to model some chromatographic peaks exhibiting peak tailing. In this situation, the general variable x is replaced by the specific variable time t and the parameter $x_0$ is replaced by $t_0$. The exponential portion may be taken to indicate a hypothetical distribution of residence times of analyte molecules on the stationary phase for a single (or small number of) of adsorption events per molecule and the Gaussian portion may be taken to represent the superimposed effects of diffusion in the mobile phase. The existence of an EMG-distribution best fit, as opposed to a Gamma-function best fit, may be taken to indicate a chromatic separation in which the analyte has lesser tendency to bind to the stationary phase.

Figure 8:
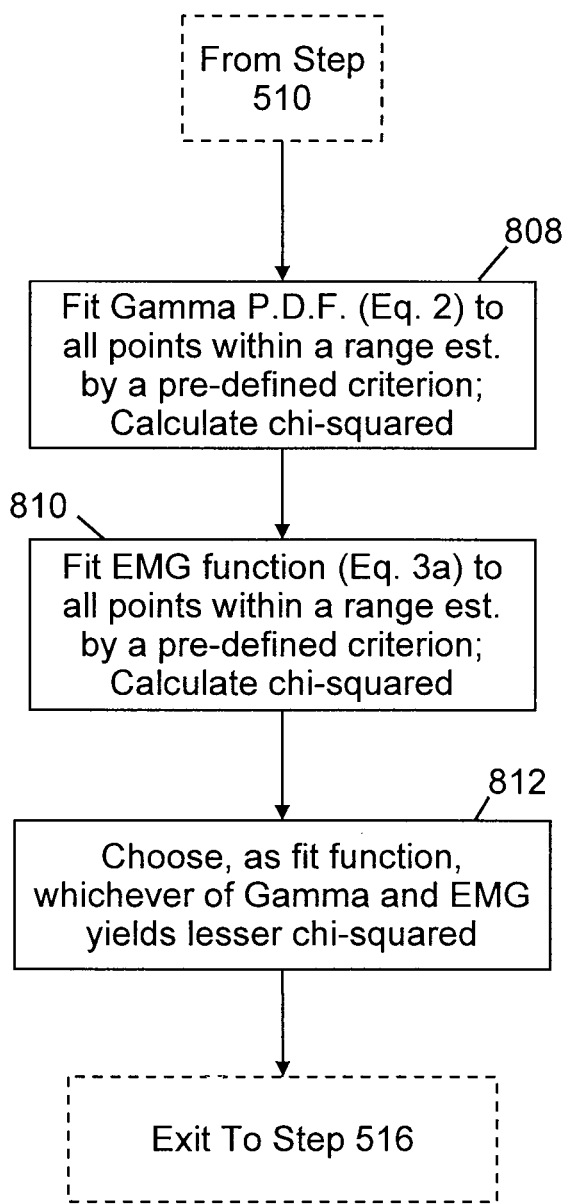
FIG. 8 is a flowchart illustrating a method for choosing between line shapes used for fitting.

FIG. 8 illustrates, in greater detail, various sub-steps that may be included in the step 512 of the method 150 (see FIG. 1 and FIG. 5) within embodiments in accordance with the present invention. More generally, FIG. 8 outlines an exemplary method for choosing between line shape forms in the modeling and fitting of an asymmetric spectral peak. The method 512 illustrated in FIG. 8 may be entered from step 510 of the method 150 (see FIG. 5).

When method 512 is entered from step 510 (see FIG. 5), the skew, S, is greater than (1+ε), because the respective "No" branch has previously been executed in each of steps 509 and 510 (see FIG. 5). For instance, if ε is set to 0.05, then the skew is greater than 1.05. When S>(1+ε), both the EMG distribution (in the form of Eq. 3) and the Gamma distribution may be fit to the data and one of the two distributions may be selected as a model of better fit on the basis of the squared difference (chi-squared statistic).

From step 808, the method 512 (FIG. 8) proceeds to step 810. In these two steps, first one line shape and then an alternative line shape is fitted to the data and a chi-squared statistic is calculated for each. The fit is performed within a range of data points established by a pre-defined criterion. For instance, the number of data points to be used in the fit may be calculated by starting with a pre-set number of points, such as 12 points and then adjusting, either increasing or decreasing, the total number of data points based on an initial estimated peak width. Preferably, downward adjustment of the number of points to be used in the fit does not proceed to less than a certain minimum number of points, such as, for instance, five points.

Alternatively, the fit may be mathematically anchored to the three points shown in FIG. 6. Alternatively, the range may be defined as all points of the peak occurring above the noise threshold. Still further alternatively, the range may be defined via some criterion based on the intensities of the points or their intensities relative to the maximum point 606, or even on criterion based wholly or in part on calculation time. Such choices will depend on the particular implementation of the method, the relative requirements for calculation speed versus accuracy, etc. Finally, in step 812, the fit function is chosen as that which yields the lesser chi-squared value. The method 512 then outputs the results or exits to step 516 of method 150 (see FIG. 5).

The determination of the best fit peak from among several potential line shapes as discussed above with reference to FIG. 8 employs a basic strategy in which the algorithm may try several or all line shapes in the "line shape library" for each and every one of the peaks. The chi-squared values computed for the best-fit peak of each type of line shape are used to decide which shape gives the best result. The inventors have, however, determined that such a calculation-intensive strategy is not always necessary since, especially with regards to chromatographic data, many peaks will have similar shapes, with certain natural peak shapes possibly predominating. Thus, in other alternative embodiments of methods in accordance with the invention, all line shapes are explored initially only for the first peak, then subsequent peaks may be fitted using the same line shape for the subsequent peaks until the chi-squared value increases by a certain predetermined limiting percentage. Once the chi-squared value has increased beyond a tolerable value, all line shapes are once again tried so as to determine a new best line shape. The new line shape is then employed for subsequent peaks until the chi-squared value once again increases by an amount greater than the predetermined percentage.

Figure 9A:
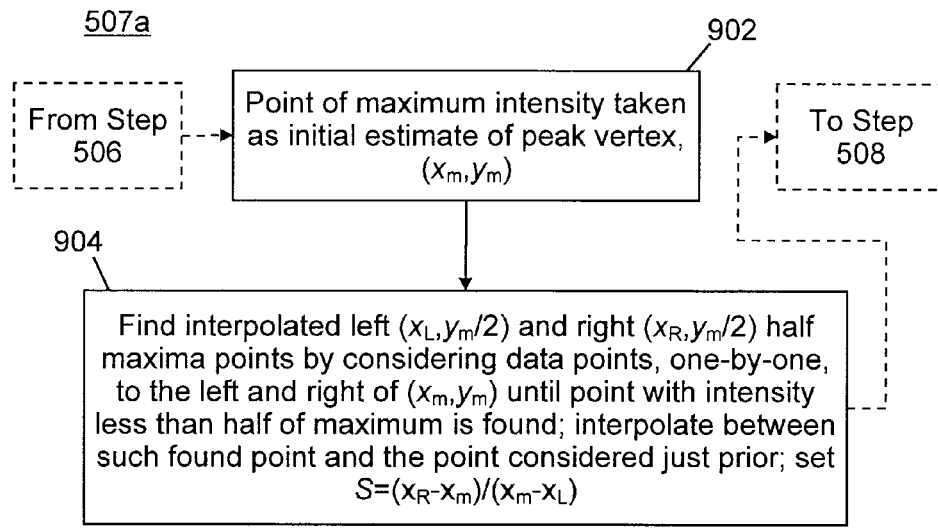
FIG. 9A is a flowchart illustrating steps for estimating coordinates of points at a peak maximum and along flanks of the peak at half-height, according to a method of the present invention.
Figure 9B:
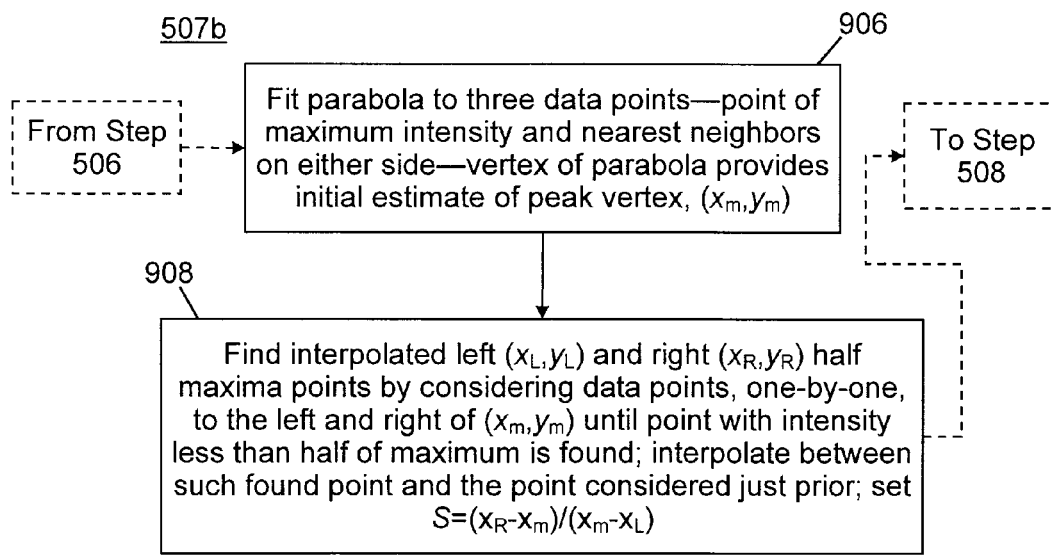
FIG. 9B is a flowchart illustrating alternative steps for estimating coordinates of points at a peak maximum and along flanks of the peak at half-height, according to a method of the present invention.
Figure 10:
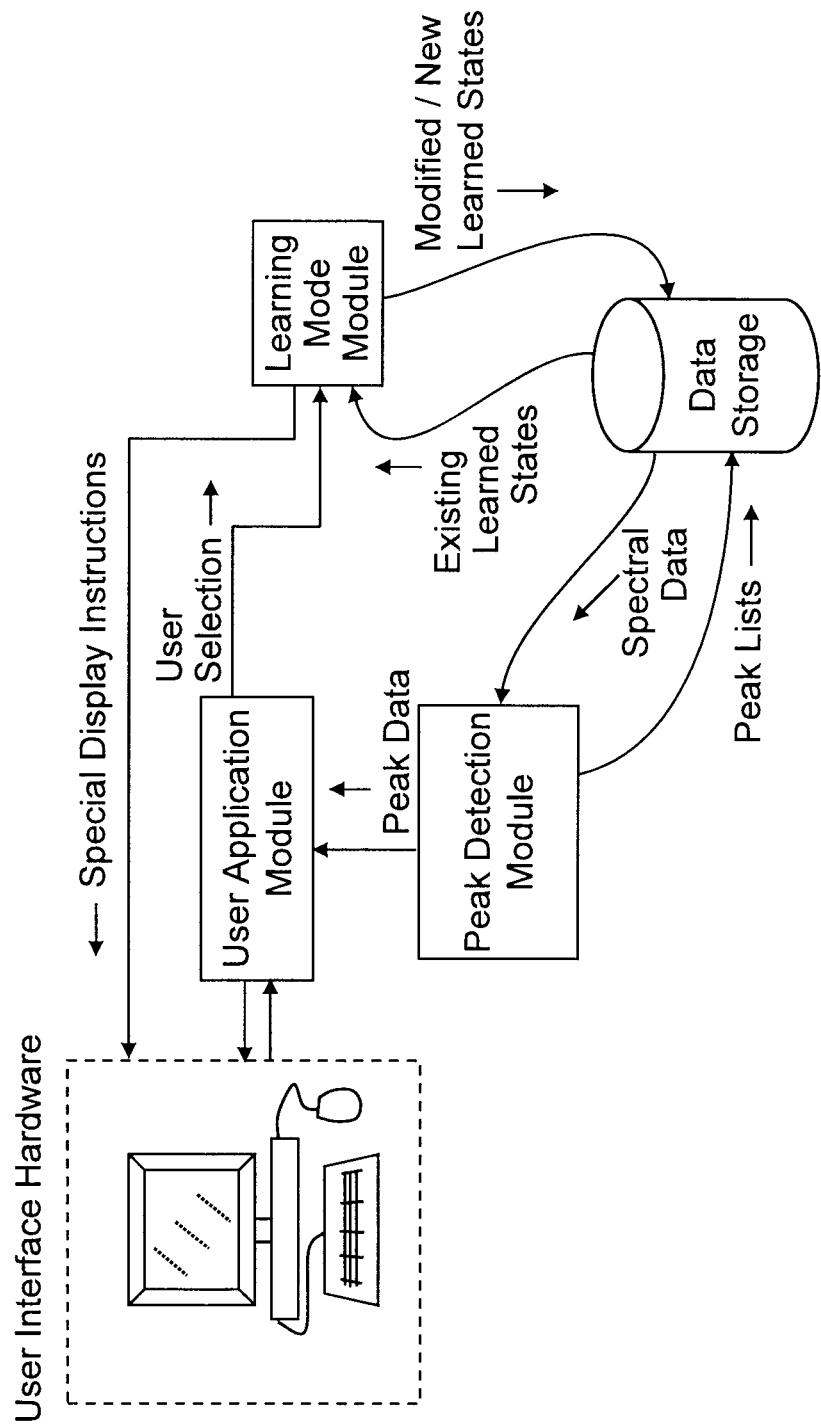
FIG. 10 is a schematic diagram of a computational system architecture for detecting peaks and modifying detection processes according to a user-initiated learning mode.

FIGS. 9A-9B are flowcharts that respectively illustrate, in greater detail, alternative sets of sub-steps that may be included in the step 507 of the method 150 (see FIG. 1 and FIG. 5) within embodiments in accordance with the present invention. More generally, FIGS. 9A and 9B illustrate steps for estimating coordinates of points at a peak maximum and along flanks of the peak at half-height, according to a first exemplary method, method 507a (FIG. 9A) as well as according to an alternative exemplary method, method 507b (FIG. 9B) in accordance with the present invention. Each of the two methods 507a (FIG. 9A) and 507b (FIG. 9B) may be entered from step 506 of method 150 (FIG. 5) and may output data or exit to step 508 of method 150. Upon detection of a peak, the point of maximum intensity (e.g., point 606 of FIG. 6) may be taken as an initial estimate of the peak vertex $(x_m, y_m)$ as in step 902 of method 507a. Alternatively, the sample of maximum intensity and its two nearest neighbors may be fit to a parabola as in step 906 of method 507b, and then the vertex of the parabola used to provide an estimate of the interpolated peak vertex (which in general does not exactly coincide with a data point of a spectrum). Next, in either step 904 of method 507a or step 908 of method 507b, the left and right half maxima of the detected peak (e.g., points 604 and 608, respectively, of FIG. 6) are estimated by examining the sample values to the left and right (respectively), scanning outward from the peak vertex until encountering a value that is less than one-half the interpolated maximum value. Interpolated values of the left and right half-maxima are determined by fitting a line to sample points whose intensities lie above and below one-half the maximum intensity and finding the x-axis coordinate (either $x_L$, or $x_R$—see FIG. 6) of the point on the line that passes through the half-maximum intensity. Then, the estimated peak skew, S, is calculated as $S=(x_R-x_m)/(x_m-x_L)$.

Returning, once again, to the method 100 as shown in FIG. 1, it is noted that, after all peaks have been fit in step 150, the next optional step, step 170 comprises refinement of the initial parameter estimates for multiple detected chromatographic peaks. Refinement comprises exploring the space of N parameters (the total number of parameters across all peaks, i.e. 4 for each Gamma/EMG and 3 for each Gaussian) to find the set of values that minimizes the sum of squared differences between the observed and model spectrum. Preferably, the squared difference may be calculated with respect to the portion of the spectrum comprising multiple or overlapped peaks. It may also be calculated with respect to the entire spectrum. The model spectrum is calculated by summing the contribution of all peaks estimated in the previous stage. The overall complexity of the refinement can be greatly reduced by partitioning the spectrum into regions that are defined by overlaps between the detected peaks. In the simplest case, none of the peaks overlap, and the parameters for each individual peak can be estimated separately.

The refinement process continues until a halting condition is reached. The halting condition can be specified in terms of a fixed number of iterations, a computational time limit, a threshold on the magnitude of the first-derivative vector (which is ideally zero at convergence), and/or a threshold on the magnitude of the change in the magnitude of the parameter vector. Preferably, there may also be a "safety valve" limit on the number of iterations to guard against non-convergence to a solution. As is the case for other parameters and conditions of methods of the invention, this halting condition is chosen during algorithm design and development and not exposed to the user, in order to preserve the automatic nature of the processing. At the end of refinement, the set of values of each peak area along with a time identifier (either the centroid or the intensity maximum) is returned. The entire process is fully automated with no user intervention required.

The step 180, in the method 100 (FIG. 1) comprises reporting peak parameters and, optionally, analyte identification and/or parameters relating to the operational state or physical characterization of the analytical instrumentation to a user. The peak parameters will, in general, be either those parameters calculated during the peak detection step 150 or quantities calculated from those parameters and may include, for each of one or more peaks, location of peak centroid, location of point of maximum intensity, peak half-width, peak skew, peak maximum intensity, area under the peak, etc. Other parameters related to signal to noise ratio, statistical confidence in the results, goodness of fit, etc. may also be reported in step 180. The information reported in step 180 may also include characterizing information on one or more analytes and may be derived by comparing the results obtained by the methods described herein to known databases. Such information may include chemical identification of one or more analytes (e.g., ions, molecules or chemical compounds), purity of analytes, identification of contaminating compounds, ions or molecules or, even, a simple notification that an analyte is (or is not) present in a sample at detectable levels.

Upon review of the reported information, a user may elect to enter learning mode in step 185. The leaning mode instructions may be implemented as a separate module—an applet or a service—that runs concurrently with a normal application displaying peak-detected data, as illustrated schematically in FIG. 10. The learning mode module may thus be independent of the application of independent of a separate peak-detection module or library that implements the parameterless peak detection steps. This learning mode module may manage the various learned states—each a collection of adjustments that may be applied to the PPD process—and has means to allow a user to create, modify, delete, and set as a default any learned state, such learned states being stored in a data storage unit (FIG. 10) for later retrieval and use. A learned state can be made part of an experimental procedure, in which situation the learned state can be applied across multiple systems and users. Alternatively, applications may be written so as to be aware of learned states and manage them without need for a separate service process.

In learning mode, the user may interact with a computer running the methods of the present invention using any suitable user interface means. Often, such user interface means will comprise a graphical user interface (GUI). Using the interface means, a user may (a) select a region or detected peak of a spectrum for which peaks have already been automatically detected and, then, (b) indicate, from a menu of choices, a general modification to be applied during subsequent automatic peak detection in the vicinity of the selected spectral region or peak. The menu that the user receives is context sensitive. If the user specifies a range where no peak is detected, the menu choices provided to the user may be, for instance, "Show rejected peaks in this region" or, "Detect a peak here" or "Extend a nearby peak to include this area". If the user specifies a peak, the menu choices may be, for instance, "Don't detect this peak", or "more aggressive peak detection in this area" or "less aggressive peak detection in this area".

When the user elects to "modify" or "create" a learned state (and specifies a name for this state), there may be a visual indication of entry into "learning mode" (for example, a change of shape of a cursor of a graphical user interface), such visual indication being maintained until learning mode is halted by the user. When the user brings up the context-sensitive menu in reference to a spectrum or chromatogram (possibly by pointing to and clicking over the data), a context menu will appear (belonging to the learning mode module) that allows the user to select an improvement desired. The program or module running the graphics display will respond to this event by reporting the user's choice for that peak back to the learning mode module. This allows the learning mode module to adjust an exit condition relating to that peak (used by the peak detection module or library) and may cause the learning mode module to request the peak-detection module or library to branch back to step 150 to re-compute peaks based on these new exit conditions.

This learning-mode feature does not allow the user to detect a peak where there is nothing but noise, or to "un-detect" a strong, well defined peak. Instead, the learning-mode module stores slight changes to the various exit conditions that control processing of the spectral data in the vicinity of the selected region or peak during execution of the peak detection module. Recall from the detailed descriptions above that, as each peak is detected, it is tested against several criteria—for instance, is the intensity signal of a candidate peak sufficiently above the background noise (step 526), how does the measured width compare to the width of the entire scan (step 508), is the residual left after this peak is removed mostly positive data, since negative peaks are not allowed (step 518), and so on. These exit conditions are stored in the information about each detected peak, and when the user requests a change in "learning mode", these learned adjustments are stored to as to be applied as the relevant peak is detected in a subsequent execution of the peak detection code.

For example, if the user had clicked over the 25th peak in the (size-ordered) list of found peaks and asked that this peak not be detected, after 24 peaks were detected the signal-to-noise (S/N) limit would be changed, for instance, from a value of 1.0 to a value just above the S/N of the undesired peak. The reverse is also true, and would have consequences for smaller peaks, which might now also pass the new criterion. For instance, if the user were to select a region with no detected peak and choose, "detect this peak", the peak detection limit would be lowered when the peak-detection module or library next processes that region of the chromatogram or spectrum, so that (for example) an additional 10% more peaks might be detected.

The feature of applying modified exit conditions at the point in peak detection when a change is needed is very powerful and easy to understand. It allows one set of conditions to be applied to strong peaks, and a modified set to be applied to weaker peaks, for example. (It also allows different settings for different regions of the data, by the user first selecting a region, then choosing a modifier to an exit condition.) Since the changes made are just enough to allow the peak in question to be affected, it is never possible to totally corrupt peak detection, say by setting the S/N threshold to 1000:1. This restriction applies because the user does not set the value; he just requests "more" or "less".

An interesting and useful feature of methods in accordance with the invention is the possibility of also reporting, in the case of chromatographic data, information related to operational state or physical characterization of the analytical instrumentation that provided the chromatographic data. For instance, derivation of parameters used in fitting Gamma distributions to peak features may provide information on fundamental properties of analyte interaction between analyte molecules and the mobile and stationary phases of a chromatographic column. Such information may include, for instance, the average number of times that molecules of a particular analyte are adsorbed on the stationary phase during their transit through the column and the average time for desorption from the stationary phase back into the mobile phase. The comparison between line shapes for different analytes (for instance, Gamma versus Gaussian versus exponentially-modified Gaussian) may provide a relative measure of the importance of adsorption versus simple diffusion in the elution of compounds from the column. A user may then use such information to adjust the composition or physical characteristics of the mobile or stationary phases so as to facilitate better chromatographic separation of certain pairs of compounds.

CONCLUSION

The end result of methods described in the preceding text and associated figures is a robust, exhaustive and general method to detect peaks and characterize spectral peaks without user-adjustable parameters. It makes no assumptions about peak shape or width, and thus can detect a wide variety of peaks, even in a single chromatogram. Additionally, a method is described for visually and interactively teaching an implementation of parameterless peak detection how to improve its accuracy and precision. This method is safe and effective in that it only allows small changes in the predefined exit conditions for peak detection and can neither force detection of a noise region as a peak, nor suppress detection of a strong, well resolved peak. It is particularly effective in improving the calculated areas for very small peaks, or peaks that have a pathological feature that prevents normal peak detection from coming to a correct result. Computer instructions according to any of the methods described above may be supplied as a computer program product or products tangibly embodied on any form of tangible computer readable medium, such computer program product or products or media on or in which they are embodied themselves being embodiments of the invention.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. For instance, although various exemplary embodiments described herein refer to peak fitting with curves of Gaussian, exponentially-modified Gaussian and Gamma distribution line shapes and with sums of Gaussian or other curves, any suitable form of line shape may be employed, depending on the particular needs of the artisan or on particular data formats or types of experiments employed. One of ordinary skill in the art would readily understand, from the discussions provided herein, how to employ the methods of the invention to fit various peak shapes using any suitable line shape. One of ordinary skill in the art would also readily understand how to modify equations presented in terms of positive and negative skew so as to fit peaks of negative and positive skew, respectively. Accordingly, many modifications may be made by one of ordinary skill in the art without departing from the spirit, scope and essence of the invention. Neither the description nor the terminology is intended to limit the scope of the invention—the invention is defined only by the claims. Any patents, patent applications or publication mentioned herein are hereby incorporated herein by reference in their respective entirety, as if set forth fully herein.

What is claimed is:

1. A method of automatically identifying and characterizing spectral peaks of a spectrum generated by an analytical apparatus comprising the steps of:
    receiving the spectrum generated by the analytical apparatus;
    automatically subtracting a baseline from the spectrum so as to generate a baseline-corrected spectrum;
    automatically detecting and characterizing the spectral peaks in the baseline-corrected spectrum;
    reporting the detected and characterized spectral peaks to a user;
    receiving a list of adjustments to be made to the detecting and characterizing step from the user;
    adjusting exit values used in the detecting and characterizing step, based on the list of adjustments; and
    repeating the automatic detecting and characterizing of the spectral peaks in the baseline-corrected spectrum using the adjusted exit values.

2. The method of claim 1, wherein the step of automatically subtracting a baseline from the spectrum so as to generate a baseline-corrected spectrum comprises automatically subtracting a baseline model curve defined by baseline model curve parameters from the spectrum, wherein said baseline model curve parameters are not input by the user.

3. The method of claim 1, wherein the step of automatically detecting and characterizing the spectral peaks in the baseline-corrected spectrum comprises automatically calculating, for at least one spectral peak, a peak model curve defined by peak model curve parameters, wherein the peak model curve provides a model fit to said at least one spectral peak, wherein said peak model curve parameters are not input by the user.

4. The method of claim 1, wherein each adjustment of the list of adjustments relates to a respective region or peak of the spectrum.

5. The method of claim 1, wherein each adjustment of the list of adjustments is chosen by the user from a finite list of possible adjustment types presented to the user.

6. The method of claim 5, wherein the finite list of possible adjustment types includes an adjustment of detecting a new peak at a specified spectral region.

7. The method of claim 5, wherein the finite list of possible adjustment types includes an adjustment of not detecting a previously detected peak.

8. The method of claim 1, further comprising the step of storing the list of adjustments for later use in conjunction with another spectrum generated by the analytical apparatus.

9. The method of claim 1, wherein the exit values relate to a minimum peak signal-to-noise ratio or a maximum peak width.

10. A non-transitory tangible computer-readable storage medium having thereon program instructions that are executable by a programmable processor, the instructions for automatically identifying and characterizing spectral peaks of a spectrum generated by an analytical apparatus, the program instructions operable to cause apparatus including the programmable processor to:
    receive the spectrum from the analytical apparatus;
    automatically subtract a baseline from the spectrum so as to generate a baseline-corrected spectrum;
    automatically detect and characterize the spectral peaks in the baseline-corrected spectrum; and
    report the detected and characterized spectral peaks to the user;
    receive a list of adjustments to be made to the detecting and characterizing step from the user;
    adjust exit values used in the detecting and characterizing step, based on the list of adjustments; and
    repeat the automatic detecting and characterizing of the spectral peaks in the baseline-corrected spectrum using the adjusted exit values.

11. The non-transitory tangible computer-readable storage medium of claim 10, wherein the instructions operable to cause the apparatus including the programmable processor to automatically subtract a baseline from the spectrum so as to generate a baseline-corrected spectrum are operable to cause the apparatus including the programmable processor to automatically subtract a baseline model curve defined by baseline model curve parameters from the spectrum, wherein said baseline model curve parameters are not input by the user.

12. The non-transitory tangible computer-readable storage medium of claim 10, wherein the instructions operable to cause the apparatus including the programmable processor to automatically detect and characterize the spectral peaks in the baseline-corrected spectrum are operable to cause the apparatus including the programmable processor to automatically calculate, for at least one spectral peak, a peak model curve defined by peak model curve parameters, wherein the peak model curve provides a model fit to said at least one spectral peak, wherein said peak model curve parameters are not input by the user.

13. The non-transitory tangible computer-readable storage medium of claim 10, wherein the instructions operable to cause the apparatus including the programmable processor to receive a list of adjustments are operable to cause the apparatus including the programmable processor to receive the list of adjustments such that each adjustment relates to a respective region or peak of the spectrum.

14. The non-transitory tangible computer-readable storage medium of claim 10, wherein the instructions operable to cause the apparatus including the programmable processor to receive a list of adjustments are operable to cause the apparatus including the programmable processor to receive each adjustment as a choice, by the user, from a finite list of possible adjustment types presented to the user.

15. The non-transitory tangible computer-readable storage medium of claim 14, wherein the finite list of possible adjustment types includes an adjustment of detecting a new peak at a specified spectral region.

16. The non-transitory tangible computer-readable storage medium of claim 14, wherein the finite list of possible adjustment types includes an adjustment of not detecting a previously detected peak.

17. The non-transitory tangible computer-readable storage medium of claim 10, wherein the program instructions are further operable to cause the apparatus including the programmable processor to:
   store the list of adjustments for later use in conjunction with another spectrum generated by the analytical apparatus.

18. The non-transitory tangible computer-readable storage medium of claim 10, wherein the instructions operable to cause the apparatus including the programmable processor to adjust exit values used in the detecting and characterizing step are operable to cause the apparatus including the programmable processor to adjust exit values that relate to a minimum peak signal-to-noise ratio or a maximum peak width.

19. A system comprising:
   at least one programmable processor unit;
   an electronic data storage unit electrically coupled to the programmable processor unit;
   user interface hardware electrically coupled to the programmable processor unit;
   a spectral peak detection executable module executing on the at least one programmable processor unit and comprising instructions operable to cause the at least one programmable processor unit to read spectral data from the electronic data storage unit and to automatically detect spectral peaks of the spectral data without receiving any parameter input from a user;
   a user application executable module executing on the at least one programmable processor unit and in communication with the spectral peak detection executable module and comprising instructions operable to cause the at least one programmable processor and the user interface hardware to present the detected spectral peaks to the user; and
   a learning mode executable module executing on the at least one programmable processor unit and in communication with the spectral application module and comprising instructions operable to cause the at least one programmable processor to receive a generate a list of adjustments to be made to exit conditions of the peak detection module instructions based on inputs from the user.

20. The system of claim 19, wherein the learning mode module further comprises instructions operable to cause the at least one programmable processor to receive a list of selections of spectral regions or spectral peaks from the user, each selection corresponding to a respective one of the adjustments.

21. The system of claim 19, wherein the learning mode module further comprises instructions operable to cause the at least one programmable processor to output the list of adjustments to the electronic data storage unit.

* * * * *